Figure 1:
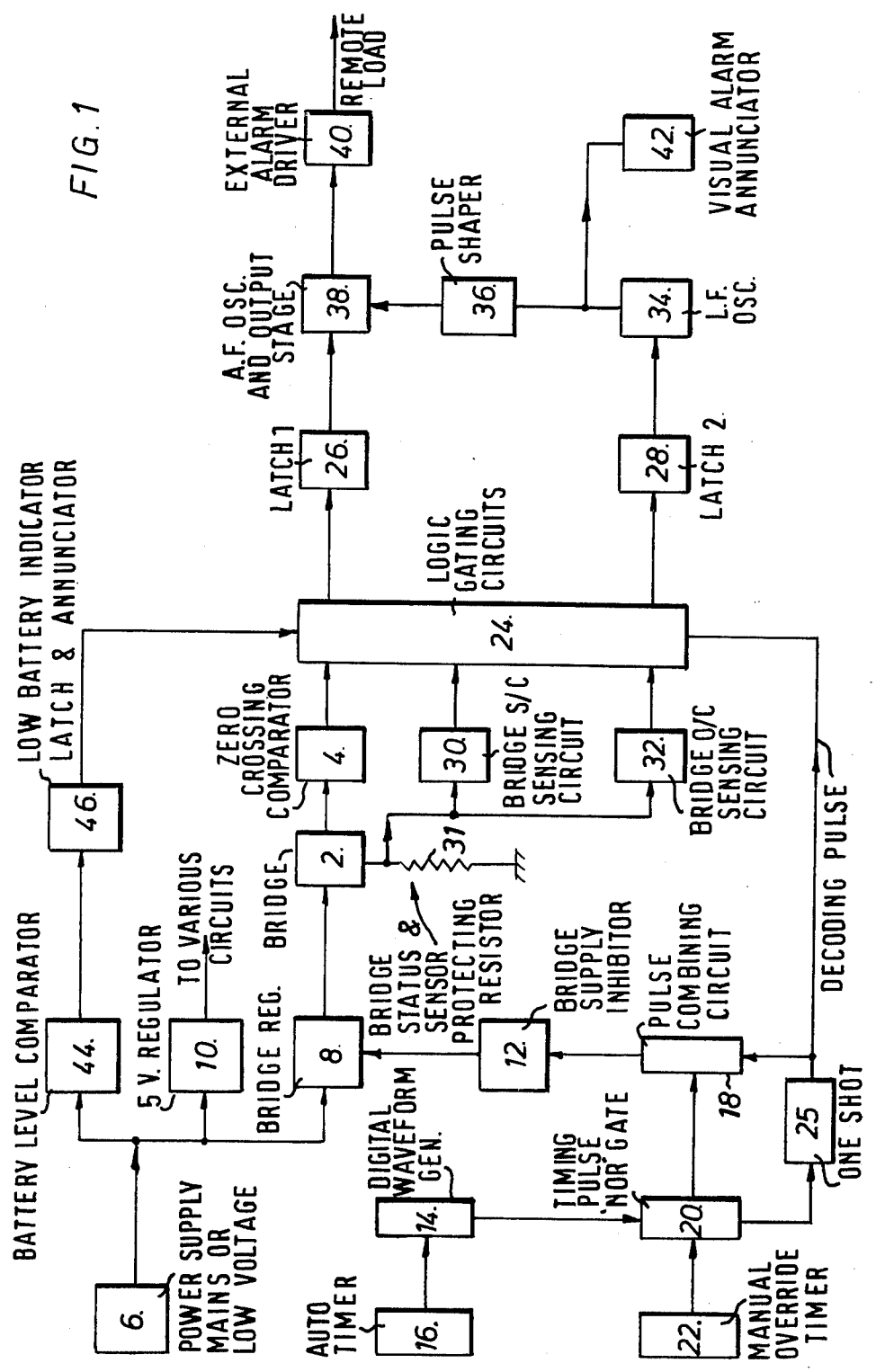

United States Patent [19]

Gotley et al.

[11] 4,020,480
[45] Apr. 26, 1977

[54] CATALYTIC DETECTING APPARATUS FOR DETECTING COMBUSTIBLE GASES AND VAPORS

[75] Inventors: Paul Gotley, Harlow; Howard Alfred Buckenham, Brentwood, both of England

[73] Assignee: Neotronics Limited, Stansted, United Kingdom

[22] Filed: Apr. 21, 1975

[21] Appl. No.: 570,073

[30] Foreign Application Priority Data

Apr. 26, 1974 United Kingdom ............ 18386/74

[52] U.S. Cl. .......................... 340/237 R; 23/254 E
[51] Int. Cl.[2] ...................................... G08B 17/10
[58] Field of Search ........... 340/228 S, 237 R, 249; 23/23, 26, 27 R, 254 E, 255 E

[56] References Cited

UNITED STATES PATENTS

| | | | |
|---|---|---|---|
| 2,857,251 | 10/1958 | Krogh | 23/255 E |
| 2,904,406 | 9/1959 | Moore | 23/254 E X |
| 3,147,465 | 9/1964 | Brown et al. | 340/237 R |
| 3,505,663 | 4/1970 | Yule | 340/249 X |
| 3,543,260 | 11/1970 | Engh | 340/228 S |
| 3,678,489 | 7/1972 | Scherban et al. | 340/237 R |
| 3,801,972 | 4/1974 | Ho Kim et al. | 340/237 R |

FOREIGN PATENTS OR APPLICATIONS 1,143,129  2/1969  United Kingdom

Primary Examiner—John W. Caldwell
Assistant Examiner—Daniel Myer
Attorney, Agent, or Firm—Cameron, Kerkam, Sutton, Stowell & Stowell

[57] ABSTRACT

Apparatus for detecting combustible gases and vapors, and comprises catalytic sensors selectively sensitive to the presence in a given environment of a potentially dangerous constituent such as a hydrocarbon gas and arranged to produce a signal representative of the presence of the constituent, a normally deactivated transducer responsive on activation to the output of the sensors and effective to produce an output signal indicative of the presence of the constituent in a concentration above a predetermined level, a pulse generating circuit arranged automatically and periodically to activate the sensors for a selected relatively short interval during which detection but not poisoning can occur and subsequently to deactivate the sensors for a relatively long period, fault detecting circuits for producing a fault signal in the event of circuit failure or impending power failure, and alarm circuitry for providing a differentiated warning in response to the fault signal and in response to the output signal.

11 Claims, 2 Drawing Figures

CATALYTIC DETECTING APPARATUS FOR DETECTING COMBUSTIBLE GASES AND VAPORS

This invention relates to detecting and/or monitoring apparatus and is particularly concerned with safety apparatus for detecting and quantitatively indicating the presence of a dangerous or contaminating constituent in an ambient gas. The invention is especially concerned with such monitors for detecting and indicating the presence of a gas such as methane which is dangerous by virtue of being able to form a potentially explosive mixture in air.

Apparatus is known for detecting the presence of methane gas as a contaminant in an ambient which generally is atmosphere. This apparatus, which is sensitive to the concentration of contaminant gas, is effective to produce a visual and/or an audible warning when the level of contamination reaches or exceeds a selected threshold. In this apparatus, the warning is intermittent and has a repetition rate representative of the contamination level above a threshold.

In this apparatus, the intermittent warning signal is of sufficient intensity to ensure a low probability of being overlooked, particularly in a harsh industrial environment, for example one producing a high intensity of background noise. The provision, in the apparatus, of a transducer whether audio or visual, capable of generating a warning of sufficient intensity to overcome any background generally requires considerable energy input and this can place a considerable drain on the electrical supply source which powers the apparatus.

In many cases the apparatus is required to monitor the concentration of contaminant gas at locations where a mains supply is inaccessible and here a suitable primary or secondary battery source must be incorporated. At best, such batteries have limited storage capacity if they are restricted in size to the point where the apparatus remains conveniently portable and accordingly provide a relatively short operating life, particularly if called upon to energise on a continuous basis the warning transducer together with the associated curcuits. It is important in such circumstances that purely monitoring use of the apparatus over a reasonable period leaves an adequate reserve of stored power available when needed for warning purposes.

It will be appreciated that in the case of battery source, whether secondary or primary, intermittent activation of the apparatus would be desirable to extend its effective operation period in the absence of contamination, and for a given operating period will provide a greater reservoir of stored power for providing a warning of contamination when this occurs. On the other hand, where mains supply is employed, intermittent activation of the apparatus will reduce the time that the sensing means are exposed to gas and thus to the risk of poisoning or other damage affecting sensitivity.

According to the present invention there is provided detecting and/or monitoring apparatus comprising sensing means selectively sensitive to the presence in a given environment of a potentially dangerous constituent and arranged to produce a signal representative of the presence of the constituent, signal translation means reponsive to the output of the sensing means and effective to produce an output signal indicative of the presence of the constituent in a concentration above a predetermined level, activating means arranged automatically and periodically to activate the sensing means for a selected interval during which detection can occur and subsequently to deactivate the sensing means; fault detecting means for producing a fault signal in the event of circuit failure or impending power failure, and alarm means for providing a warning in response to the fault signal and in response to said output signal.

Preferably, modulating means are provided to modulate the output of the sensing; the fault signal is then expediently a continuous, unmodulated signal, whereby to differentiate between the presence of gas and the occurrence of a fault or failure.

Moreover, nowadays the catalytic transducer type of gas detectors is used on a wide scale. Such a transducer is essentially a metal coil acting as a resistance thermometer whicn senses the heat that is evolved when a combustible gas reacts with atmospheric oxygen on the surface of a heated catalyst, or on the surface of the coil itself when the material of the coil is itself the catalyst of the oxidation process. The increase in heat and the attendant increase in resistance is convertible into an electrical output signal. Suitable catalytic transducers are known from U.S. Pat. No. 3,092,799. When using such catalytic transducers in the present invention, the further advantages accrue that short intermittent operation improves the service life of the transducers (the cost of which is far from negligible); calibration intervals may be increased; long-term stability of operation is improved and the relative shortness of transducer energisation, be it by a battery source or a mains supply, assists in reducing the risk of "poisoning" of the transducers by contaminants. Such "poisoning" may be permanent and irreversible, e.g. due to silicon derived from hot machine oil.

Still further, it is known to provide two catalytic transducers arranged in adjacent arms of a balanced Wheatstone bridge circuit, one transducer being sensitive to the presence of gas while the other one being rendered insensitive to gas. Such circuits in general are operated with the bridge balanced for zero output in the absence of gas. These known arrangements suffer from bridge offset drift problems. Intermittent operation helps to overcome, or at least mitigate, such drift problems.

Moreover, in such arrangements the differential output from the bridge is then amplified in subsequent circuitry. This has the severe disadvantage that any residual drift will be amplified and may in certain cases be interpreted as an output signal indicating the presence of gas. In contrast, according to a preferred embodiment of the invention the apparatus includes a bridge circuit arranged with an output offset from zero in one direction such that the presence of gas causes the output to move in the opposite direction, through zero, and this zero-crossing is detected by a high-quality zero-crossing comparator, e.g. an amplifier of substantially infinite gain, adapted to produce a logic output. In this way the apparatus is rendered substantially independent of zero drift.

The sensing means may include a bridge circuit containing two sensors in adjacent arms, there being a voltage-dividing resistor connected in series with the effective resistance of the bridge circuit for protecting the sensors and for sensing any departure from predetermined conditions at the bridge circuit, fault-detecting logic circuits being connected to said resistor.

In a preferred embodiment of the invention, there are mode changing means for enabling the intermittent activation to be overridden to produce continuous operation of the sensing means; in this mode it is arranged that the modulation varies with gas concentration so that the apparatus is then usable for locating the source of gas, i.e. the region of highest gas concentration.

Where it is desired to initiate activation of the sensing means without waiting for the automatic deactivation period to terminate, the apparatus may include manual override means for overriding the automatic cycle of activation-deactivation periods. In the overridden mode operation is random, i.e. as long as is desired, which can be achieved by continued activation of the override means. In this way, the ambient can be sampled for contamination or failure by an operator without any waiting period.

Suitably, the same means that produces the warning of contamination may be used to produce the warning of failure of the circuit or abnormal power level.

Preferably, a testing device is connectable to the sensing means to stimulate the presence of said constituent. This enables the self-checking of the apparatus to be carried out whenever desired.

In one variant, the apparatus is powered by a low voltage DC power supply, and there is provided means, including a warning device, for monitoring the output voltage of said power supply.

Figure 2:
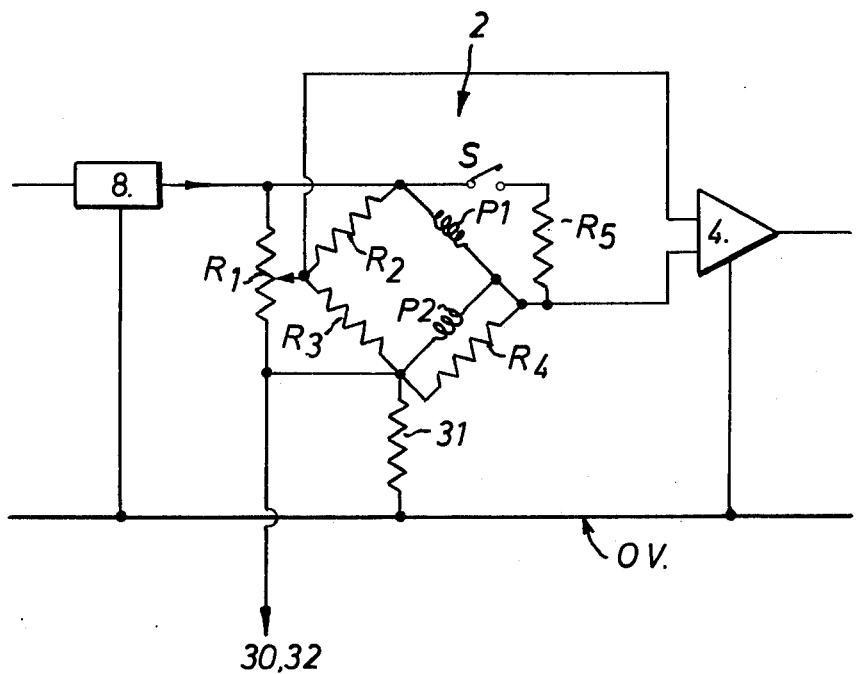

Advantageously, the activating means including a timer for generating pulses of a duration sufficient to energise and stabilise the sensing means, and a one-shot generator which is connected to the timer and is adapted to generate pulses at the end of the pulses received from the timer, the duration of the one-shot generator pulses being independent of the duration of the pulses generated by the timer; and logic gating circuits connected to receive the pulses from the one-shot generator which circuits gate signals from the signal translation means and the fault-detecting means simultaneously. The invention will now be described, by way of example only, with reference to the accompanying drawings, in which:

FIG. 1 is a schematic circuit diagram of an apparatus for detecting and/or monitoring hydrocarbon gas in air, and FIG. 2 is a detail thereof.

Referring to the drawings, the apparatus includes a sensing section incorporating sensing means, in this preferred embodiment two catalytic transducer-type sensors, P1, P2, one of which is sensitive to the presence of hydrocarbon gases in the air under test. Methane is one of the most frequent pollutants and hereafter the description will be so restricted. The transducers P1, P2 are arranged in adjacent arms of a bridge circuit 2 arranged to produce a small output to one side of zero or balance when the concentration of methane is below a predetermined threshold level. The presence of methane is reflected in a change in output in the other direction, the output crossing zero, with the output level being representative of the level of contamination.

As can be seen in FIG. 2, the bridge 2 essentially comprises two catalytic transducers P1, P2 and two fixed resistors R2, R3 in its four arms. A resistor R4 shunts the transducer P2 and is adjustable on test for temperature compensation. A variable resistor R1 is connected in the bridge input, as shown, to act as a potentiometer the output of which is used as a reference input for a comparator 4 described below. A bridge status and transducer protecting resistor 31, further referred to below, is connected between the junction of transducer P1 and resistor R3 and earth. The resistor 31 and the effective resistance of the bridge 2 together constitute a potential divider.

The output of bridge 2 is applied to the comparator 4, which is a zero-crossing detector functioning as an amplifier of infinite gain adapted to switch sharply at the instant where precise balance occurs and to produce a logic output of 0 to 1 level according to the presence or absence of gas. Illustratively, the comparator comprises an integrated circuit amplifier, type LM311, as manufactured by the National Semiconductor Corp.

The bridge 2 obtains its operating current from a conventional source 6 which may be dry batteries, rechargeable batteries or a mains step-down transformer having a secondary winding feeding a rectifier and smoothing capacitor network. The source 6 delivers some 2.5 volts to the bridge 2 by way of a conventional stabilising circuit indicated at 8. In the arrangement with which the invention is particularly concerned, the power is derived from primary or secondary batteries, the mains power supply in the case of secondary batteries being optionally retained for recharging purposes. A further stabilising circuit 10 supplies 5 volts to the positive rail of the apparatus from which current is derived to power the various modules hereinafter described.

The output of stabilising circuit 8 comprises essentially a power output transistor, which can be biased to cut off by a bridge supply inhibitor circuit 12.

In this invention, the inhibitor circuit 12 is arranged automatically to supply intermittent operating current to bridge 2 as a sequence of pulses of some 10 seconds' duration every four minutes of elapsed time. The 10 seconds' pulse duration activates only the bridge 2 and its output terminates and ensures stable operative conditions during the tail end of the pulse period when the output of the comparator 4 is sampled.

A digital waveform generator 14, which contains a binary counter, receives pulses of 10-second duration every 30 seconds of elapsed time from an auto-timer 16 containing an R-C network and converts these pulses to a repetition rate of 10 seconds in every 240 seconds. Illustratively, the generator 14 comprises a digital waveform generator as manufactured by Signetics Corp., under their type No. 7493. The timing pulses are applied to the inhibitor circuit 12 by way of a pulse-combining circuit 18 and a "NOR" gate 20 which provides access between the inhibitor circuit 12 and a manual override timer 22. The timers 16 and 22 each may illustratively comprise a Signetics type NE555 timer, and the combining circuit may illustratively be formed of a 7402 IC module and a 7400 IC module of Signetics. The timer 22 is totally independent of the auto-timer 16, and is normally inoperative. The timer 22, which contains an R-C network, can activate the inhibitor circuit 12 to supply current to the bridge 2 for a 10-second period at any point in the time cycle of operation controlled by the generator 14 and can eliminate the waiting time of up to four minutes, if a random test is required.

While many catalytic transducers require between 5 to 8 seconds to stabilize, same others require less time. To same battery drain, the R-C networks of the timers 16 and 22 may be adjusted or replaced for such transducers.

In certain operational conditions it may be desirable to alter the ratio of the duration of the activated and deactivated periods of the transducers to provide faster or slower sampling times. The deactivation period of the transducers may also be changed very conveniently by altering the divide ratio of the binary counter in the digital waveform generator 14.

To ensure that the output of the comparator 4 is sampled for gas testing only at the tail end of the 10-second activation period when operating conditions have stabilised, it is applied to the warning control circuit by way of logic gating circuits 24 which are gated by a pulsed "one-shot" generator 25 controlled in response to the output from gate 20. The operations of the circuits 24, as will be explained below, are performed by parts of two type 7402 and one type 7400 IC modules, as manufactured by Signetics Corp. The duration of the pulses of the generator 25 is independent of the duration of the pulses of the timer 16. Generator 25 provides at the end of the 10-second gate output a pulse of about one microsecond's duration. during which the circuits 24 provide access between latches 26, 28 on the one hand, and the comparator 4, a battery level comparator 44, as well as a bridge shortcircuit sensing circuit 30 and an open-circuit 32 on the other hand. It will therefore be appreciated that the period of 1 μsec of the one-shot is unlikely to coincide with any likely external interference pulse; moreover, as it occurs only once every four minutes, response to spurious interference signals is substantially eliminated, or at least considerably reduced. This can be important particularly where the bridge and the comparator 4 are remote from each other. The generator or "one shot" multiplier 25, as well as a coupled NOR gate 20, are formed of IC modules, type 7402, of Signetics Corp.

As indicated in FIG. 2, the sensing circuits 30 and 32 respectively derive their inputs from the bridge status and sensor protecting resistor 31. The sensing circuits 30, 32 illustratively in the form of commonly-available transistors, are effective to produce a logic output in the event of a short-circuit or open-circuit condition at the bridge 2. They enhance the safety of the apparatus by providing a warning of failure in either of these modes. The resistor 31 also serves to protect the catalytic transducers p1, p2, during warm-up, its resistance being chosen to be approximately equal to that of the combined "cold" resistance of the transducers, and thus diverts from the transducers a considerable portion of the output current of the bridge regulator 8. The "hot" resistance of a typical catalytic transducer is 50–75% more than the "cold" resistance.

FIG. 2 also shows a switch S connected across transducer P1, with a gas-simulating resistor R5. The switch S is a test switch allowing full electrical fault testing of the circuit even in the absence of any by closing the switch, the resistor R5 will shunt the transducer P1. The value of resistor R5 is so chosen that it will provide an offset equivalent to the presence of gas marginally above the threshold level, thus causing the bridge output to cross the zero DC level.

Latches 26 and 28, illustratively formed from parts of a 7400-type Signetics IC module, are effective to hold and to provide a continuous output in the event of a pulsed input applied through the logic gating circuitry 24 from the detector or by sensing circuits 30 or 32.

The logic gating circuits 24 are arranged so that latches 26 and 28 are activated by a logic signal from the comparator 4 indicating a level of contamination above a selected threshold. With latch 28 operating in response to a gas presence only, a low frequency oscillator 34 is activated to modulate, via a pulse shaper 36, an audio frequency oscillator and output stage 38 which includes a gas warning indicator or transducer such as a loudspeaker (not shown). The oscillator circuit 38 may illustratively take the form of an IC module tone generator, type NE555, of Signetics Corp. The oscillator 34 illustratively comprises a type NE555 IC module of Signetics Corp. and desired, to drive an additional, external warning device, e.g. a klaxon.

Latch 26, in contrast to latch 28, is energised in the event of a gas or a fault signal; thus in the event of a fault signal, oscillator 38 only is energised to provide an unmodulated output so that a warning signal of different mode is obtained from the loudspeaker in this case. The warning of excess gas concentration or of a fault condition are thus of different modes and can easily be distinguished. The alarm signals are maintained even after the "gas-presence" or fault condition has been cleared, so that a positive act of resetting is required. Moreover, if the gas-presence condition is still in existence after resetting, at the end of the next sensing period, irrespective of how initiated, the gas alarm will come "on" again.

For certain applications, a two-level alarm is provided, corresponding to e.g. 1 and 5% concentrations of methane, respectively. This simply necessitates appropriate duplication of certain circuit elements such as resistors in the bridge and the zero-crossing comparator, together with suitable coupling to the logic gating circuits and differentiated means for producing audio and/or visual alarms.

It will be appreciated that while the invention has been specifically described with a reference to a gas contamination warning signal, it may equally be applied to other warning systems, for example to providing an indication when the pH level of a liquid effluent exceeds a selected danger limit.

As has been referred to above, the logic gating circuitry 24 is responsive also to the battery level comparator 44 connected to a low battery indicator 46 which provide an indication of battery failure or reduction of capacity. The indicator illustratively takes the form of an IC module, type 7400 of Signetics Corp. The reference input of comparator 44 is so chosen that the battery voltage is sensed at a level which still provides sufficient capacity to enable the rest of the circuit to produce a warning of low battery for an appreciable period, in case the apparatus is left unattended by an operator for a while. An associated bistable or other electronic latch holds the circuit in a set condition and provides a suitable differentiated indication. Even if the battery were to recover, the fault signal remains.

Resetting means are provided to reset all latches and the alarm to normal conditions at the initial siwtch-on.

It will be appreciated from the foregoing description that the apparatus according to this invention provides a very high degree of self-checking by assigning a unique combination of logic outputs from the various parts of the apparatus in the cases where, respectively, the apparatus is functioning correctly and no gas is being detected, where gas is being detected, and where there is a fault either in a circuit component or in the power supply. Any deviation from the preset conditions is automatically arranged to produce a warning.

It is also to be noted that the circuits employed are essentially digital and not analogue in character, thereby eliminating or reducing drift problems associated with known analogue devices.

We claim as our invention:

1. Detecting apparatus comprising:
   a. normally inactive sensing means selectively sensitive to the presence in a given environment of an extraneous constituent and operative to produce an electrical signal representative of the presence of the constituent, said sensing means requiring a period of time after actuation to achieve normal operation;
   b. electrical signal translation means responsive on activation to the signal of the sensing means to produce an output signal indicative of the presence of the constituent in a concentration above a predetermined level,
   c. activating means connected to the sensing means and arranged automatically and periodically to:
      1. generate pulses of a duration sufficient to energize and stabilize the sensing means to normal operation, and
      2. subsequently to deactivate the sensing means for a period which is at least as long as the said interval of activation;
   d. fault detecting means for producing a fault signal in the event of circuit failure;
   e. alarm means for providing a warning in response to the fault signal and in response to the output signal;
   f. a one-shot generator means connected to the activating means to generate a one-shot pulse at the end of the pulses received from the activating means, the duration of the pulses of said one-shot generator means being independent of the duration of the pulses generated by the activating means and being insufficiently long to coincide with an external interference signal; and
   g. logic gating circuits connected to receive the pulses from said one-shot generator means and to gate signals from said signal translation means and said fault-detecting means simultaneously.

2. Apparatus according to claim 1, wherein manual override means is connected to the sensing means to energize, on actuation, the sensing means, thereby to terminate the deactivated period of the latter.

3. Apparatus according to claim 1, wherein the ratio of duration of the deactivated and activated periods of the sensing means is at least 10:1.

4. Apparatus according to claim 1, wherein said sensing means includes a bridge circuit, two sensors in adjacent arms of the bridge circuit, a voltage-dividing resistor connected in series with the effective resistance of the bridge circuit for protecting said sensors and for sensing any departure from predetermined conditions at the bridge circuit, and two fault-detecting logic circuits having a respective input and a respective output, each input being connected to said resistor, said circuits being effective to produce an output signal in logic form in response, respectively, to a short circuit and to an open circuit in the bridge circuit.

5. Apparatus according to claim 1, wherein said apparatus is powered by a low-voltage DC power supply, and further comprises means including a warning device for monitoring the output voltage of the said power supply.

6. Detecting apparatus comprising:
   a. normally inactive sensing means selectively sensitive to the presence in a given environment of an extraneous constituent and operative to produce an electrical signal representative of the presence of the constituent, said sensing means requiring a period of time after actuation to achieve normal operation and including a catalyst to promote oxidation of the constituent, but susceptible to poisoning;
   b. electrical signal translation means responsive on activation to the signal of the sensing means to produce an output signal indicative of the presence of the constituent in a concentration above a predetermined level;
   c. activating means arranged automatically and periodically to:
      1. activate said sensing means for an interval of a duration sufficient to energize and stabilize the sensing means to normal operation and for detection to occur, but insufficient for the sensing means to be poisoned, and
      2. subsequently to deactivate the sensing means for a period which is at least as long as the said interval of activation;
   d. fault detecting means for producing a fault signal in the event of circuit failure;
   e. alarm means for providing a warning in response to the fault signal and in response to said output signal; and
   f. mode changing means selectively connected to the sensing means, said mode changing means including means for overriding the periodical activating means and for continuously energizing the sensing means.

7. Apparatus according to claim 6, wherein, for continuous operation, modulating means is connected to the signal translation means to modulate the output signal of the latter at a repetition rate indicative of the concentration of the said constituent.

8. Apparatus according to claim 6, wherein said activating means includes a timer for generating pulses of a duration sufficient to energize and stabilize the sensing means, and a one-shot generator which is connected to the timer and in use generates pulses at the end of the pulses received from the timer, the duration of said one-shot generator pulses being independent of the duration of the pulses generated by the timer; a pulse combining circuit connected to receive and logic gating circuits connected to receive the pulses from said one-shot generator which circuits gate signals from said signal translation means and said fault-detecting means simultaneously.

9. Apparatus according to claim 8, wherein the duration of the pulses from said one-shot generator is chosen to minimize the probability of coincidence with an external interference signal.

10. Detecting apparatus comprising:
    a. normally inactive sensing means selectively sensitive to the presence in a given environment of an extraneous constituent and operative to produce an electrical signal representative of the presence of the constituent, said sensing means requiring a period of time after actuation to achieve normal operation and including a catalyst to promote oxidation of the constituent, but susceptible to poisoning, the sensing means including an unbalanced bridge circuit, two catalytic transducers in adjacent arms of the bridge circuit, and a zero-crossing comparator connected to the output side of the bridge and operative to produce an output signal in logic form when the bridge circuit is balanced on sensing said constituent;

b. electrical signal translation means responsive on activation to the signal of the sensing means to produce an output signal indicative of the presence of the constituent in a concentration above a predetermined level;

c. activating means arranged automatically and periodically to:
 1. activate said sensing means for an interval of a duration sufficient to energize and stabilize the sensing means to normal operation and for detection to occur, but insufficient for the sensing means to be poisoned, and
 2. subsequently to deactivate the sensing means for a period which is at least as long as the said interval of activation;

d. fault detecting means for producing a fault signal in the event of circuit failure; and e. alarm means for providing a warning in response to the fault signal and in response to said output signal.

11. Apparatus according to claim 10, wherein a resistor and a switch are connected across one of said catalytic transducers, said resistor having a value to provide an offset equivalent to the presence of said constituent above the predetermined level to cause said bridge circuit to balance and trigger said zero-crossing comparator.

* * * * *